(12) United States Patent
Shen

(10) Patent No.: US 12,371,518 B2
(45) Date of Patent: Jul. 29, 2025

(54) MINIMALLY SWELLABLE BIOCOMPATIBLE MEMBRANE AND PREPARATION METHOD THEREOF

(71) Applicant: SUZHOU ZHONGXING MEDICAL TECHNOLOGY CO., LTD., Suzhou (CN)

(72) Inventor: Wei Shen, Suzhou (CN)

(73) Assignee: SUZHOU ZHONGXING MEDICAL TECHNOLOGY CO., LTD., Jiangsu (CN)

( * ) Notice: Subject to any disclaimer, the term of this patent is extended or adjusted under 35 U.S.C. 154(b) by 9 days.

(21) Appl. No.: 17/914,311

(22) PCT Filed: Mar. 31, 2022

(86) PCT No.: PCT/CN2022/084392
§ 371 (c)(1),
(2) Date: Sep. 23, 2022

(87) PCT Pub. No.: WO2022/228022
PCT Pub. Date: Nov. 3, 2022

(65) Prior Publication Data
US 2024/0209130 A1    Jun. 27, 2024

(30) Foreign Application Priority Data
Apr. 29, 2021  (CN) .................. 202110475319.X

(51) Int. Cl.
*C08F 212/08* (2006.01)
*A61B 5/145* (2006.01)
*A61B 5/1486* (2006.01)
*B01D 71/28* (2006.01)
(Continued)

(52) U.S. Cl.
CPC ........ *C08F 212/08* (2013.01); *A61B 5/14532* (2013.01); *A61B 5/1486* (2013.01);
(Continued)

(58) Field of Classification Search
CPC .... B01D 17/44; B01D 71/441; B01D 71/281; B01D 71/5211; B01D 71/78; B01D 71/76;
(Continued)

(56) References Cited

U.S. PATENT DOCUMENTS 5,284,140 A * 2/1994 Allen .................. B01D 71/76
204/415
2008/0034972 A1   2/2008 Gough et al.
(Continued)

FOREIGN PATENT DOCUMENTS

CN           1813020 A     8/2006
CN         106397727 A     2/2017
(Continued)

*Primary Examiner* — Luan V Van
*Assistant Examiner* — Kaylee Tseng
(74) *Attorney, Agent, or Firm* — SZDC Law PC

(57) ABSTRACT

The present invention relates to a biocompatible membrane, specifically to a minimally swellable biocompatible membrane and the preparation method thereof. The preparation method of the minimally swellable biocompatible membrane comprises the following steps: synthesis of a copolymer containing a skeleton and a hydrophilic group, the introduction of a biocompatible property, the preparation of a biocompatible membrane solution, and the coating of the biocompatible membrane. The present invention can effectively regulate glucose, and has high biocompatibility (long service life) as well, thereby improving the sensitivity, accuracy, reproducibility, stability, specificity and anti-interference ability in a continuous glucose monitoring (CGM) system, prolonging the life time of the CGM, and greatly reducing the cost of the CGM.

9 Claims, 3 Drawing Sheets

(51) Int. Cl.
  *B01D 71/44* (2006.01)
  *B01D 71/52* (2006.01)
  *B01D 71/78* (2006.01)
  *C08F 290/12* (2006.01)
  *G01N 27/30* (2006.01)
(52) U.S. Cl.
  CPC ......... *B01D 71/281* (2022.08); *B01D 71/441* (2022.08); *B01D 71/5211* (2022.08); *B01D 71/78* (2013.01); *C08F 290/124* (2013.01); *G01N 27/301* (2013.01); *G01N 27/308* (2013.01)
(58) Field of Classification Search
  CPC ............... B01D 2325/58; C08F 212/08; C08F 290/124; A61B 5/14532; A61B 5/1486; G01N 27/301; G01N 27/308; G01N 27/26; C08L 25/08
  See application file for complete search history.

(56) References Cited

U.S. PATENT DOCUMENTS

| | | | |
|---|---|---|---|
| 2011/0305872 A1* | 12/2011 | Li | C08F 291/00 428/141 |
| 2012/0132525 A1* | 5/2012 | Liu | C07F 15/0026 525/327.1 |
| 2016/0045147 A1 | 2/2016 | Ouyang et al. | |
| 2023/0323079 A1* | 10/2023 | Gao | C08L 83/06 525/332.5 |

FOREIGN PATENT DOCUMENTS

| | | | | |
|---|---|---|---|---|
| CN | 113325049 A | 8/2021 | | |
| CN | 113521399 A | 10/2021 | | |
| WO | WO-2005034852 A2 * | 4/2005 | | A61K 31/70 |
| WO | 2020158451 A1 | 8/2020 | | |

* cited by examiner

MINIMALLY SWELLABLE BIOCOMPATIBLE MEMBRANE AND PREPARATION METHOD THEREOF

This application is the National Stage Application of PCT/CN2022/084392, filed on Mar. 31, 2022, which claims priority to Chinese Patent Application No. 202110475319.X, filed on Apr. 29, 2021, which is incorporated by reference for all purposes as if fully set forth herein.

FIELD OF THE INVENTION

The present invention relates to a biocompatible membrane, specifically to a minimally swellable biocompatible membrane and the preparation method thereof.

BACKGROUND OF THE INVENTION

Continuous glucose monitoring (CGM) systems developed rapidly in recent years have brought good news to diabetics. They allow diabetic people to monitor their blood glucose more conveniently and effectively. It can continuously detect blood glucose in real time, and has gradually become a powerful tool for blood glucose regulation. The performance of a biocompatible membrane, as a main component of the biosensor of the CGM and the only interface of the CGM in direct contact with a living body, directly determines the performance and life time of the CGM. Existing CGMs are developed based on the first- or second-generation biosensing technology. The CGMs based on the first-generation biosensing technology for continuous glucose monitoring include G5 and G6 of Dexcom and Guardian and iPro2 of Medtronic, and have the working principle that they indirectly monitor glucose by electrochemically detecting the hydrogen peroxide generated by the reduction of oxygen during the catalytic oxidation of glucose by glucose oxidase. Since the CGMs developed based on the first-generation biosensing technology relies on the oxygen (a natural mediator for the catalytic oxidation of glucose by glucose oxidase) in body fluids (e.g. tissue fluid or blood) to monitor glucose, and the content of oxygen in body fluids (0.2-0.3 mmol/L) is much lower than that of glucose (5-10 mmol/L), the biocompatible membrane of the CGM system must be able to maximally allow the passage of oxygen while effectively regulate the passage of glucose in addition to its high biocompatibility. It is well known that oxygen is hydrophobic compared with glucose, so the biocompatible membrane must also be highly hydrophobic. However, since the main component of tissue fluid is water, the requirement of high hydrophobicity poses great challenges for the design of the biocompatible membrane. Although exploration has been made for more than 20 years, the performance of this kind of CGMs is still far from ideal in continuous glucose monitoring. For example, Guardian and iPro2 made by Medtronic still need to be calibrated twice a day and have a life time of only one week.

At the end of last century, Heller et al. (Accounts of Chemical Research 23 (1990) 128-134) found that, with the introduction of redox substances—artificial redox mediators (redox polymers, or small redox molecules such as ferricyanide, ferrocene and the derivatives thereof, and other transition metal complexes)—into biosensing membranes, glucose oxidase can achieve electron exchange with substrate electrodes via the redox substances—the second-generation biosensing technology. The second-generation biosensing technology developed based on this principle is currently widely used in biosensors, especially glucose biosensors, including the glucose biosensors for CGMs, such as FreeStyle Libre made by Abbott Diabetes Care. Since the second-generation biosensing technology realizes direct electrochemical detection of glucose by introducing the synthetic redox mediator into the biosensor, glucose detection can be realized at very low potentials through the molecular design and optimization of the redox mediator, thus greatly improving the anti-interference ability of the CGMs. Because this kind of glucose monitoring system performs direct electrochemical detection of glucose through the artificial redox mediator, its sensitivity is significantly improved. On the other hand, although the direct electrochemical detection of glucose is realized by introducing the synthetic redox mediator, oxygen, as the natural mediator for the catalytic oxidation of glucose by glucose oxidase, inevitably participates in the catalytic oxidation of glucose and becomes an important interfering factor in glucose monitoring. In order to further improve the performance of such CGMs, various biocompatible membranes have been introduced, which on one hand eliminates the interference of oxygen to a great extent, and on the other hand extends the monitorable range of glucose. In view of the significant difference in hydrophilicity between glucose and oxygen, high hydrophilicity is a basic characteristic of such biocompatible membranes. Therefore, hydrogels or polymers mainly composed of hydrogels have become the choices for such biocompatible membranes (U.S. Patents including U.S. Pat. Nos. 9,777,307, 9,668,685, 9,014,774, and 9,042,954). Although such biocompatible membranes can regulate glucose very efficiently, they are difficult to achieve effective and precise simultaneous regulation of oxygen and glucose. For effective regulation, it is necessary to significantly increase the thickness of the biocompatible membranes. However, an excessively thick biocompatible membrane will directly lead to an excessively long response time of the CGM, resulting in a severe hysteresis, which greatly reduces the accuracy of the CGM. Moreover, with hydrogels having a major property that they may swell to a considerable extent in an aqueous environment, excessive swelling will greatly increase the volume of the sensor and weaken the mechanical strength and adhesion of the biocompatible membrane (U.S. Pat. No. 9,668,685), which may result in parts of the biocompatible membrane being torn off from the CGM and left in human body when the CGM is removed. In addition, there is a chemical crosslinking reaction in the existing formulations of the hydrogel-based biocompatible membrane, which greatly shortens the pot life of the biocompatible membrane solution and virtually increases the production cost of the CGM (U.S. Patents including U.S. Pat. Nos. 9,777,307 and 9,042,954). More seriously, with the increase of use time, there are more and more chemical crosslinking reactions, and the viscosity of the biocompatible membrane solution increases, which seriously affect the consistency of the CGM.

CONTENTS OF THE INVENTION

In order to overcome the shortcomings of the first- and second-generation biosensing technologies, the present invention provides a minimally swellable biocompatible membrane and the preparation method thereof, and applies the minimally swellable biocompatible membrane to a glucose biosensor based on the third-generation biosensing technology, namely the electrochemical activation technology of oxidoreductase, so as to effectively improve the sensitivity, accuracy, reproducibility, stability, specificity and anti-interference ability of the CGM, prolong the life time of the CGM, and greatly reduce its cost.

According to the technical solution of the present invention, the preparation method of the minimally swellable biocompatible membrane comprises the following steps:

A. Synthesis of a copolymer containing the hydrophobic skeleton and hydrophilic moieties;

A1. dissolving a hydrophobic monomer and a monomer containing a hydrophilic group in ethanol, and removing oxygen with nitrogen;

A2. adding azodiisobutyronitrile, and placing the obtained solution in an airtight container for reaction; and A3. separating and purifying to obtain a precipitate, which is the copolymer containing the hydrophobic skeleton and hydrophilic moieties;

B. The introduction of the biocompatible property and preparation of a biocompatible membrane solution B1. dissolving the copolymer containing the hydrophobic skeleton and hydrophilic moieties in ethanol; and B2. adding a biocompatible substance and a crosslinking agent, mixing thoroughly, and then reacting in a water bath to obtain the biocompatible membrane solution; and C. coating of a biocompatible membrane coating the biocompatible membrane solution on the biosensor directly or after diluting the biocompatible membrane solution, and drying at room temperature to form a membrane, thus obtaining the minimally swellable biocompatible membrane.

Further, the hydrophobic monomer is styrene, vinylpyridine, acrylate or acrylamide and the derivatives thereof.

Further, the monomer containing a hydrophilic group is vinylpyrrolidone, vinylized polyethylene glycol, an acrylate with an ethylene glycol group, or an olefin with an ethylene glycol group.

Further, the separating and purifying operation in A3 is specifically as follows: adding water to precipitate the copolymer containing the hydrophobic membrane skeleton and hydrophilic group, centrifuging, removing the supernatant, adding ethanol to dissolve the precipitate, and repeating for 2-6 times.

Further, the biocompatible substance is a high-molecular-weight polymer with high hydrophilicity and biocompatibility or an aminated monomer with high biocompatibility.

Further, the high-molecular-weight polymer with high hydrophilicity and biocompatibility is polyethylene oxide, a copolymer containing polyethylene oxide, polypropylene oxide, a copolymer containing polypropylene oxide, polyvinyl alcohol, polylactic acid, hyaluronic acid and the derivatives thereof, chitosan and the derivatives thereof, cellulose and the derivatives thereof, alginic acid and the derivatives thereof, or aminated polyethylene glycol; and the monomer with high biocompatibility is choline, betaine, amino acid, ethylene oxide, or propylene oxide.

Further, the crosslinking agent is triglycidyl p-aminophenol, glycidyl ether and the derivatives thereof, polypropylene glycol glycidyl ether and the derivatives thereof, polyethylene glycol diglycidyl ether and the derivatives thereof, or glutaraldehyde.

Further, the biocompatible membrane solution is dissolved in methanol, ethanol, propanol, isopropanol, water, N,N-dimethylacrylamide, dimethyl sulfoxide, sulfolane, tetrahydrofuran or dioxane for storage.

In a second aspect, the present invention provides a minimally swellable biocompatible membrane prepared by any of the above-mentioned preparation methods.

In a third aspect, the present invention provides a glucose biosensor comprising the above-mentioned minimally swellable biocompatible membrane.

The present invention has the following beneficial effects: The present invention can effectively regulate glucose, and has high biocompatibility (long life time) as well, thereby effectively improving the sensitivity, accuracy, reproducibility, stability, specificity and anti-interference ability of the CGM, prolonging the life time of the CGM, and greatly reducing its cost.

Figure 1:
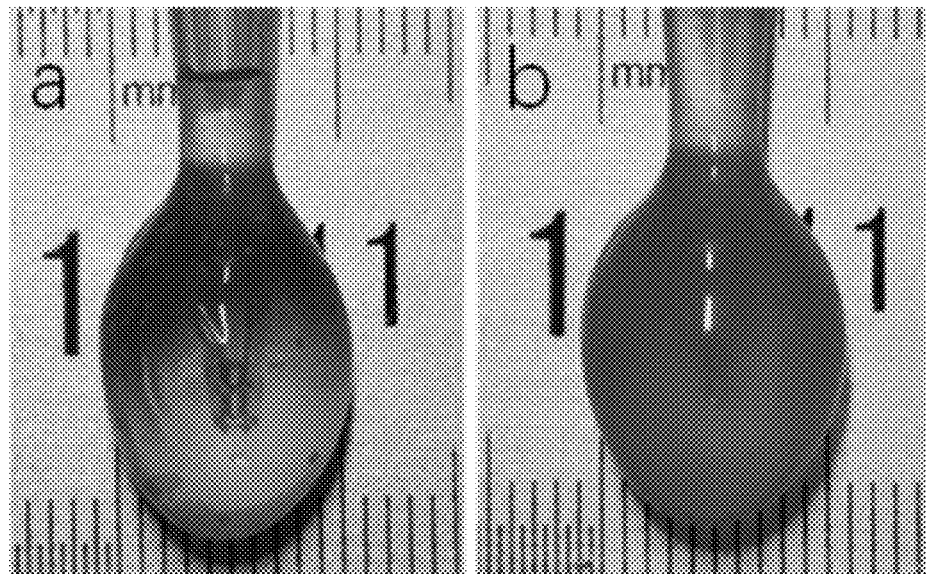
FIG. 1 shows the change in volume of the biocompatible membrane before and after being soaked.

Description of reference numerals: 1. Biocompatible membrane; 2. carbon counter electrode; 3. polyethylene terephthalate substrate; 4. carbon working electrode; 5. glucose sensing membrane; and 6. silver/silver chloride reference electrode.

DETAILED DESCRIPTION OF THE EMBODIMENTS

The present invention will be further described below in conjunction with the accompanying drawings and specific examples, so that those skilled in the art can better understand and implement the present invention, while the examples are not intended to limit the present invention.

Example 1

The preparation method of the minimally swellable biocompatible membrane comprised the following steps:

A. Synthesis of a copolymer containing the hydrophobic skeleton and hydrophilic moieties.

A1. mixing 10-100 mL styrene, 5-50 mL vinylpyrrolidone and 20-200 mL absolute ethanol, and removing oxygen with nitrogen for 20-60 min;

A2. adding 10-200 mg azodiisobutyronitrile, placing the obtained solution in an airtight container, and reacting at 40-70° ° C. for 12-24 h;

A3. adding 500-5000 mL water to precipitate the copolymer of styrene and vinylpyrrolidone, and centrifuging for separation;

A4. adding ethanol to the precipitate obtained in step A3 to dissolve the precipitate, then adding 500-5000 mL water for precipitation, and centrifuging; and A5. repeating step A4 for 2-6 times, drying the obtained precipitate under vacuum at 60-120° C. for 12-40 h to obtain the polymer containing the hydrophobic skeleton and hydrophilic moieties;

B. introduction of the biocompatible property and preparation of a biocompatible membrane solution B1. dissolving the copolymer containing the hydrophobic skeleton and hydrophilic moieties in ethanol to obtain a 100-300 mg/mL solution; and B2. adding 10-30 mg/mL aminated polyethylene glycol and 0.2-5 mg/mL triglycidyl p-aminophenol crosslinking agent, mixing thoroughly, then reacting in a water bath at 60° C. for 20-60 min to obtain the biocompatible membrane solution. After the crosslinking reaction, adding 5-20 mg/mL amino acid to stop the crossing linking reaction, so as to obtain a highly stable solution, and dissolving the biocompatible material in methanol, ethanol, propanol, isopropanol, water, N,N-dimethylacrylamide, dimethyl sulfoxide, sulfolane, tetrahydrofuran or dioxane for storage and indefinite use; and C. coating of a biocompatible membrane coating the biocompatible membrane solution evenly on the biosensor by a dip coating method or a spin coating method directly, or evenly on the biosensor by a spraying method after dilution of the biocompatible membrane solution, drying at room temperature to form a membrane, then repeating the coating, and drying for 1-10 times.

Examples 2-3

On the basis of Example 1, the vinylpyrrolidone in step A1 was replaced by vinylized polyethylene glycol, an acrylate with an ethylene glycol group, and an olefin with an ethylene glycol group, respectively.

Examples 4-12

On the basis of Example 1, the styrene in step A1 was replaced by vinylpyridine, acrylate, acrylamide, methacrylamide, diacetone acrylamide, cinnamamide, N-isopropylacrylamide, N-phenylacrylamide, and N,N-dimethylacrylamide, respectively.

Examples 13-32

On the basis of Example 1, the aminated polyethylene glycol in step B2 was replaced by polyethylene oxide, a copolymer containing polyethylene oxide, polypropylene oxide, a copolymer containing polypropylene oxide, polyvinyl alcohol, polylactic acid, hyaluronic acid and the derivatives thereof, chitosan and the derivatives thereof, cellulose and the derivatives thereof, alginic acid and the derivatives thereof, aminated choline, aminated betaine, aminated amino acid, aminated ethylene oxide, aminated propylene oxide, and aminated vinylpyrrolidone, respectively.

Examples 33-38

On the basis of Example 1, the triglycidyl p-aminophenol in step B2 was replaced by glycidyl ether, polypropylene glycol glycidyl ether and the derivatives thereof, polyethylene glycol diglycidyl ether and the derivatives thereof, and glutaraldehyde, respectively.

Test Example 1

Biocompatible membrane beads above 10 mm were prepared by the dip-pull method from the biocompatible membrane solution obtained in Example 1, and then they were soaked in a PBS buffer solution containing 10 mmol/L glucose for 7 days. The volumes of the biocompatible membrane beads before and after soaking are compared, with the results shown in FIG. 1. It can be seen that the biocompatible membrane beads, after being soaked in the PBS buffer solution containing 10 mmol/L glucose for 7 days, only have less than 10% of swelling, which fundamentally ensures that the biocompatible membrane will not be significantly affected in the mechanical properties by swelling after being implanted. Besides, because the crosslinking reaction is completely terminated by amino acids, their stability and pot life are greatly improved, making it possible to prepare CGMs with high consistency.

Application Example 1

Figure 2:
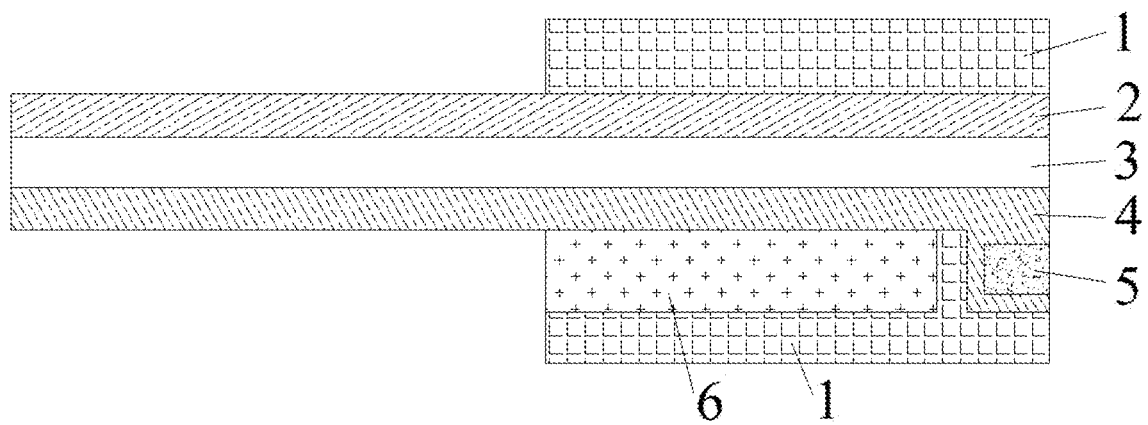
FIG. 2 schematically shows the structure of the glucose biosensor in Example 1.
Figure 3:
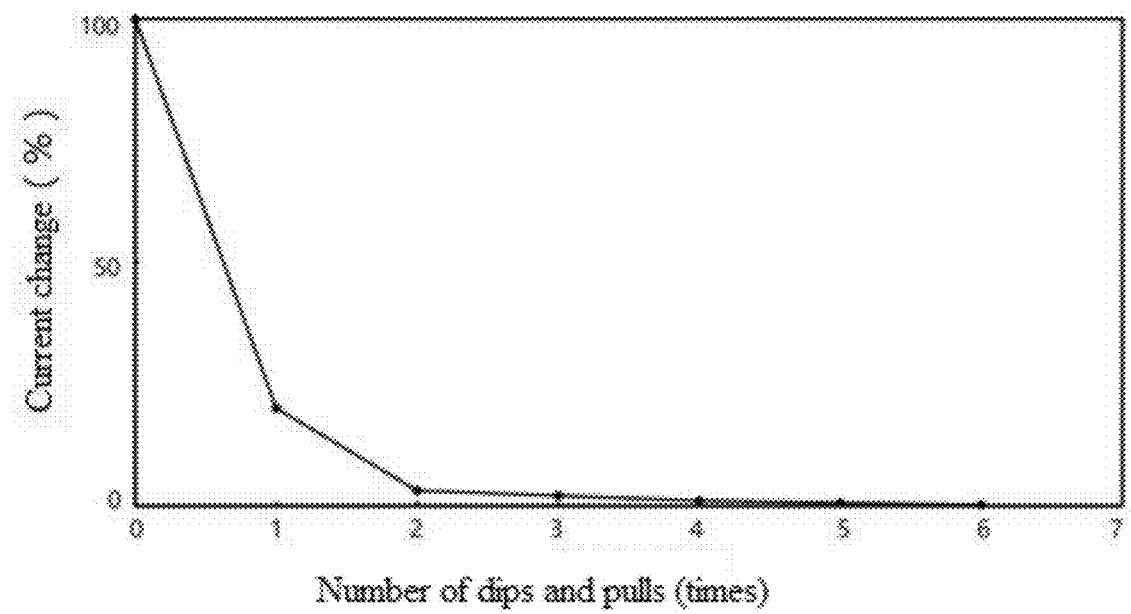
FIG. 3 shows the relationship between the current and the number of coatings of the glucose biosensor in Example 1 in a PBS buffer solution containing 10 mmol/L glucose.

The biocompatible membrane solution obtained in Example 1 was evenly coated on the glucose biosensors as shown in FIG. 2 or 3 by the dip coating method, the glucose biosensors comprising a polyethylene terephthalate substrate 3, a carbon counter electrode 2 and a carbon working electrode 4 respectively covering the two sides of the polyethylene terephthalate substrate 3, a glucose sensing membrane 5 coated on the carbon working electrode 4, a silver/silver chloride reference electrode 6 disposed outside the carbon working electrode 4, and a biocompatible membrane 1 covering the carbon counter electrode 2, the silver/silver chloride reference electrode 6 and the carbon working electrode 4. These glucose biosensors were then dried to form a membrane in a strictly controlled environment. After the solvent evaporated completely, the surface of these glucose biosensors were completely coated with biocompatible membranes. In order to increase the thickness of the biocompatible membrane, the above process could be repeated at will, usually 3-4 times, to achieve the required thickness. Since this biocompatible membrane was formed through multiple membrane-forming processes, its final performance of regulating oxygen and glucose could reach the desired level very conveniently and effectively through optimization of the thickness of the membrane (by controlling the number of dip coatings) and the formulation of the biocompatible membrane solution.

Figure 4:
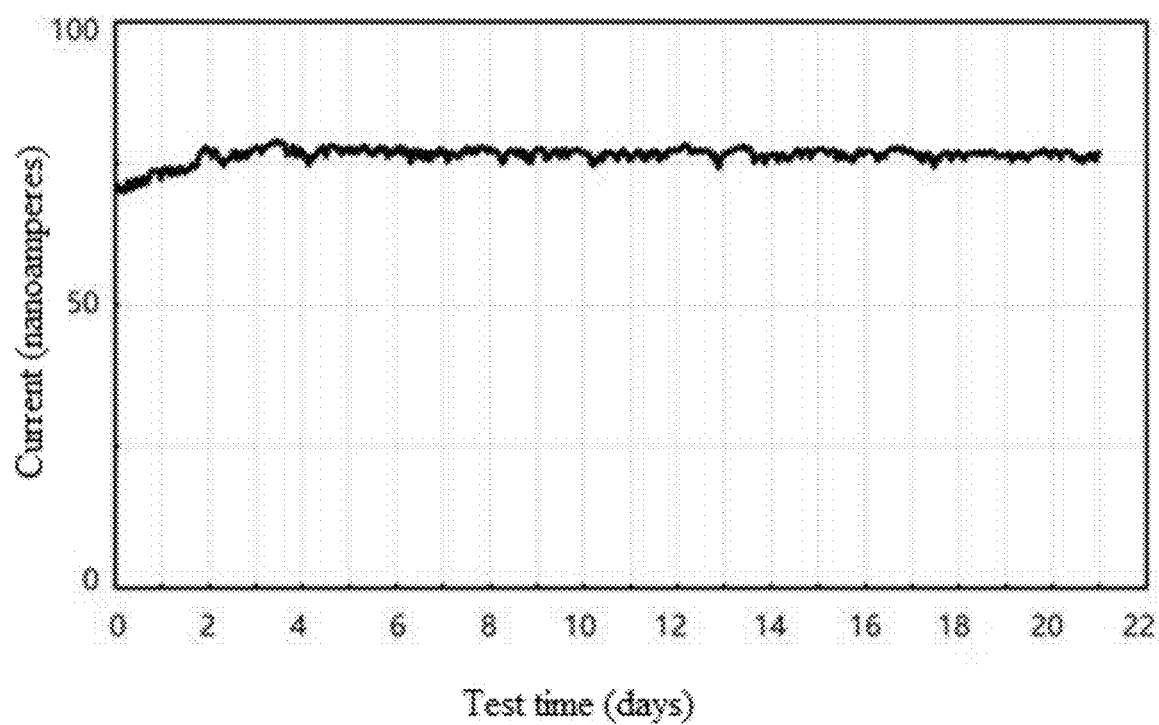
FIG. 4 shows the change in stability of the glucose biosensor coated with a three-layer biocompatible membrane in Example 1 in a PBS buffer solution containing 20 mmol/L glucose.

As shown in FIG. 3, when the glucose biosensor was completely coated with the biocompatible membrane, its catalytic oxidation current for glucose decreased exponentially with the increase of the thickness of the membrane (the increase of the number of dip coatings); after four cycles of dip coating and drying, the current of the glucose biosensor decreased to less than 1% of the original. This result shows that the biocompatible membrane of the present invention can regulate glucose very efficiently. Further, the glucose biosensor coated with the biocompatible membrane exhibited excellent stability during continuous testing for up to three weeks (as shown in FIG. 4).

Figure 5:
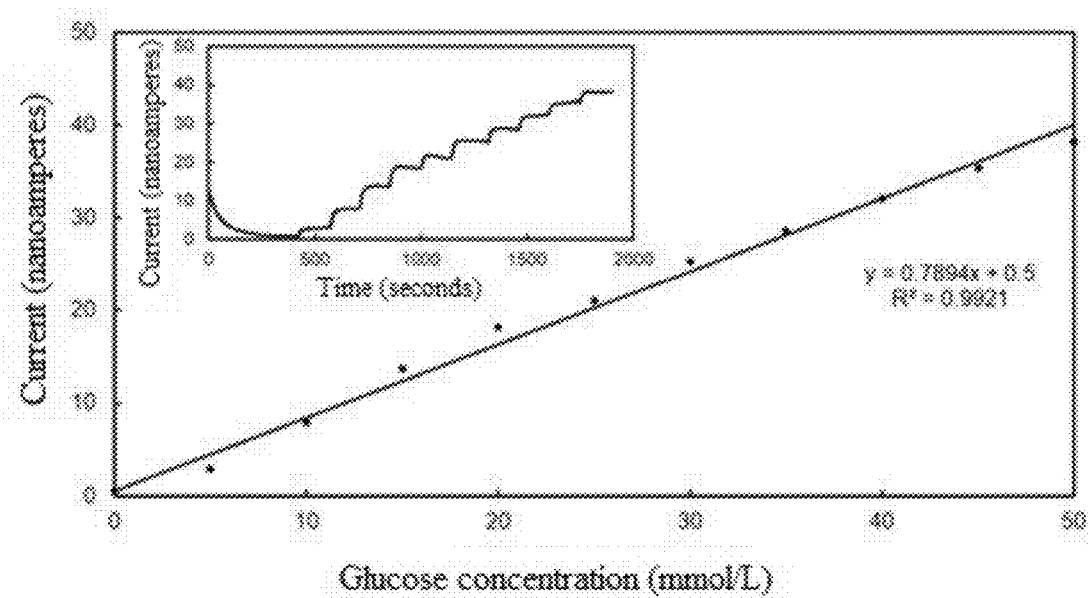
FIG. 5 shows the relationship between the current and glucose concentration of the glucose biosensor coated with a four-layer biocompatible membrane in Example 1 (the change gradient of the glucose concentration: 5 mmol/L).

Precise regulation of oxygen and glucose with high stability has been successfully achieved by covering the glucose biosensors with a biocompatible membrane; however, in order to obtain a glucose biosensor with high accuracy, reproducibility and stability, it is necessary to ensure that these sensors have a wide enough linear response range, which can be achieved by optimizing the biocompatible membrane on the glucose biosensors. For example, compared with the glucose biosensor without being coated with any biocompatible membrane, the current of the glucose biosensor that had been subjected to four cycles of coating was well regulated by the biocompatible membrane; in addition, the monitorable range of glucose was successfully extended from 10 mmol/L to 50 mmol/L (as shown in FIG. 5), the glucose biosensor coated with the biocompatible membrane has the widest linear response range so far for in vivo use, fully satisfying the needs of diabetics for glucose monitoring.

Figure 6:
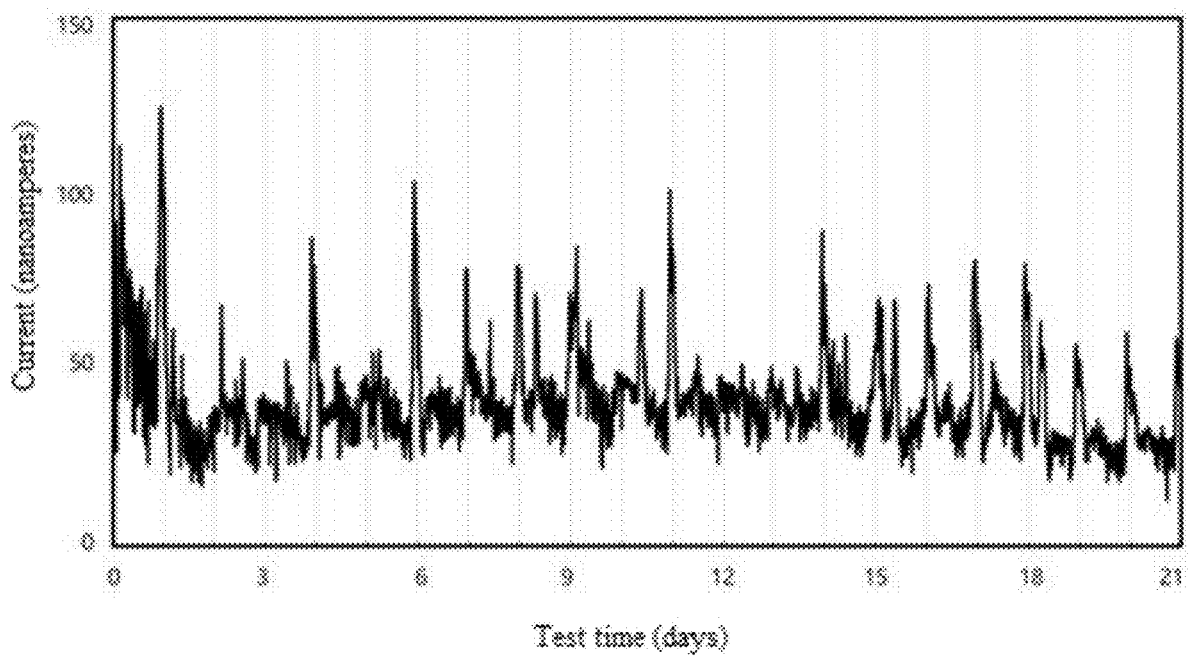
FIG. 6 shows an in vivo test of the glucose biosensor coated with the three-layer biocompatible membrane in Example 1 in a CGM.

Although the biocompatible membrane of the present invention exhibits superior performance in in vitro tests as demonstrated by the above experimental results, its performance in in vivo monitoring is the most powerful proof of its biocompatibility. Therefore, on the basis of the in vitro work, the glucose biosensor coated with the biocompatible membrane was applied to an CGM, which showed no significant decrease in sensitivity (baseline) in a 21-day in vivo trial (as shown in FIG. 6), the longest life time of CGM ever manufactured; moreover, the glucose concentration results obtained by the CGM were highly consistent with those obtained by the finger blood glucose testing.

To sum up, by being coated with the minimally swellable biocompatible membrane of the present invention, the glucose biosensor developed based on the third-generation biosensing technology can regulate glucose very effectively and accurately; more importantly, the existence of this biocompatible membrane significantly extends the monitorable range of glucose, greatly improves the stability and biocompatibility of the glucose biosensor in vivo, which fully meets the requirements of calibration-free (factory-calibrated) CGMs, laying a solid foundation for the mass production of the calibration-free CGMs. In addition, this biocompatible membrane can also be applied to other implantable continuous monitoring systems, for example, continuous monitoring of lactic acid and blood ketone.

Obviously, the above examples are only for clear description, rather than limiting the embodiments. For those of ordinary skill in the art, other various alterations or modifications can also be made on the basis of the above description. It is unnecessary and impossible to enumerate all the embodiments here. However, the obvious alterations or modifications thus derived are still within the protection scope of the present invention.

The invention claimed is:

1. A preparation method of a swellable biocompatible membrane, characterized in that the method comprises the following steps:
   A. synthesis of a copolymer containing a hydrophobic skeleton and hydrophilic moieties;
   A1. dissolving a hydrophobic monomer and a monomer containing a hydrophilic group in ethanol, and removing oxygen with nitrogen;
   A2. adding azodiisobutyronitrile, and placing the obtained solution in an airtight container for reaction; and
   A3. separating and purifying to obtain a precipitate, which is the copolymer containing the hydrophobic skeleton and hydrophilic moieties;
   B. introduction of biocompatibility and preparation of a biocompatible membrane solution;
   B1. dissolving the copolymer containing the hydrophobic skeleton and hydrophilic moieties in ethanol; and
   B2. adding a biocompatible substance and a crosslinking agent, mixing thoroughly, and then reacting in a water bath to obtain the biocompatible membrane solution; and
   C. coating of the biocompatible membrane;
   coating the biocompatible membrane solution on a biosensor directly or after dilution of the biocompatible membrane solution, and drying at room temperature to form a membrane, thus obtaining the swellable biocompatible membrane,
   wherein the separating and purifying operation in A3 is specifically as follows: adding water to precipitate the copolymer containing the hydrophobic membrane skeleton and hydrophilic moieties, centrifuging, removing a supernatant, adding ethanol to dissolve the precipitate, and repeating for 2-6 times.

2. The preparation method of a swellable biocompatible membrane according to claim 1, characterized in that: the hydrophobic monomer is styrene, vinylpyridine, acrylate, or acrylamide and the derivatives thereof.

3. The preparation method of a swellable biocompatible membrane according to claim 1, characterized in that: the monomer containing a hydrophilic group is vinylpyrrolidone, vinylized polyethylene glycol, an acrylate with an ethylene glycol group, or an olefin with an ethylene glycol group.

4. The preparation method of a swellable biocompatible membrane according to claim 1, characterized in that: the biocompatible substance is a polymer with hydrophilicity and biocompatibility or an aminated monomer with high biocompatibility.

5. The preparation method of a swellable biocompatible membrane according to claim 4, characterized in that: the high-molecular-weight polymer with high hydrophilicity and biocompatibility is polyethylene oxide, a copolymer containing polyethylene oxide, polypropylene oxide, a copolymer containing polypropylene oxide, polyvinyl alcohol, polylactic acid, hyaluronic acid and the derivatives thereof, chitosan and the derivatives thereof, cellulose and the derivatives thereof, alginic acid and the derivatives thereof, or aminated polyethylene glycol; and the monomer with high biocompatibility is choline, betaine, amino acid, ethylene oxide, or propylene oxide.

6. The preparation method of a swellable biocompatible membrane according to claim 1, characterized in that: the crosslinking agent is triglycidyl p-aminophenol, glycidyl ether and the derivatives thereof, polypropylene glycol glycidyl ether and the derivatives thereof, polyethylene glycol diglycidyl ether and the derivatives thereof, or glutaraldehyde.

7. The preparation method of a swellable biocompatible membrane according to claim 1, characterized in that: the biocompatible membrane solution is dissolved in methanol, ethanol, propanol, isopropanol, water, N,N-dimethylacrylamide, dimethyl sulfoxide, sulfolane, tetrahydrofuran, or dioxane for storage.

8. A swellable biocompatible membrane prepared by the method according to claim 1.

9. A glucose biosensor, characterized in that: it includes the swellable biocompatible membrane according to claim 8.

* * * * *